United States Patent [19]

Naser et al.

[11] Patent Number: 4,840,166
[45] Date of Patent: Jun. 20, 1989

[54] SHOCK WAVE SOURCE WITH INCREASED DEGREE OF EFFECTIVENESS

[75] Inventors: Georg Naser, Zirndorf; Helmut Reichenberger, Eckental; Hubert Schwark, Erlangen, all of Fed. Rep. of Germany

[73] Assignee: Siemens Aktiengesellschaft, Berlin and Munich, Fed. Rep. of Germany

[21] Appl. No.: 31,334

[22] Filed: Mar. 26, 1987

[30] Foreign Application Priority Data

Apr. 1, 1986 [DE] Fed. Rep. of Germany ....... 3610837

[51] Int. Cl.$^4$ .............................................. A61B 17/22
[52] U.S. Cl. ................................... 128/24 A; 128/328
[58] Field of Search ............... 128/24 A, 328; 367/147

[56] References Cited

U.S. PATENT DOCUMENTS

| 2,559,227 | 7/1951 | Rieber | 128/24 A |
| 4,281,550 | 8/1981 | Erikson | 128/660 |
| 4,608,979 | 9/1986 | Breidenthal et al. | 128/328 |
| 4,669,472 | 6/1987 | Eisenmenger | 128/328 |

FOREIGN PATENT DOCUMENTS

| 01300709 | 1/1985 | European Pat. Off. . |
| 3312014 | 10/1984 | Fed. Rep. of Germany . |
| 58-085694 | 5/1983 | Japan . |
| 534448 | 2/1940 | United Kingdom . |

OTHER PUBLICATIONS

Journal of the Acoustical Society of America, No. 2, Feb. 1986, pp. 566–570; Entitled: "Ultrasonic Nonlinear Parameters and Sound Speed of Alcohol-Water Mixtures".

Primary Examiner—Ruth S. Smith
Attorney, Agent, or Firm—Lawrence C. Edelman

[57] ABSTRACT

A shock wave source, especially useful for a lithotriptor, has a pressure source for the generation of a pressure wave impulse, a focusing device for focusing the pressure wave pulse, and a seal diaphragm for coupling the pressure wave pulse into the body of a patient, perhaps via a coupling body placed between the seal diaphragm and the patient. The seal diaphragm and the focusing device of the pressure source form a space which serves as a prepassage. The prepassage space is filled with a liquid substance which has a high B/A ratio and an acoustic impedance less than or equal to that of water. The advantage of this configuration is that the pressure wave pulse can be built up very rapidly in its course through the space. At a given point in the space, with the selection of the above-mentioned substances, as compared to water, a given minimum value of the quotient amplitude/build-up time of the pressure wave pulse can be achieved inspite of a reduced output amplitude at the pressure source. Consequently, the life expectancy of the pressure source is higher and less stress is placed on the patient by the acoustic energy. Thus, the degree of effectiveness of the lithotriptor is increased.

3 Claims, 1 Drawing Sheet

SHOCK WAVE SOURCE WITH INCREASED DEGREE OF EFFECTIVENESS

BACKGROUND OF THE INVENTION

Field of the Invention

The invention relates to a shock wave source, particularly, useful for a lithotriptor, including a pressure source for the generation of a pressure wave pulse, a focusing device for focusing the pressure wave pulse and a seal diaphragm for coupling the pressure wave pulse into a body.

Such a shock wave source is know, for example, from German Patent Publication No. 33 28 051. As shown therein, a pressure source is provided in the form of a shock wave tube which transmits a pressure wave pulse. The pressure wave pulse traverses a prepassage space to a focusing device which is, for example, fashioned as a lens. After the focusing device, the pulse traverses a coupling space before it is coupled into the body of a patient via a seal diaphragm. In this case, it is used for lithotripsy, that is, the fragementation of concrements, such as kidney stones.

A shock wave source of the above mentioned kind is furthermore known from German Patent Publication No. 33 12 014. There, the pressure source and the focusing device are combined. The coil of the pressure source is of concave shape so as to generate an already focused pressure wave pulse. The focusing device has a natural or geometric focus at the site wherein the concrement to be fragmented is placed. By the time it has reached the focus, the pressure wave pulse has developed into a shock wave pulse.

Experimentation has shown that in general the following applies: If up to a distance of approximately one-half wavelength from the geometric focus no shock wave has formed, on the basis of diffraction limitation, no further focusing and thus no formation of shock wave up to the focus can take place. The wavelength results thereby from the duration of the fundamental oscillation associated with the instantaneous pressure wave pulse. Experiments have further shown that the pressure wave pulse must have a given minimum value for the ratio of amplitude to build-up time at the focusing device in order that a shock wave can form at all. In order to achieve this minimum value for the quotient given by the geometry and customary filling with water of the prepassage space, it is necessary to generate a pressure wave pulse with a relatively high amplitude at the site of the focusing device. From the point of view of the equipment, this is decidedly a disadvantage for the life expectancy of the pressure source, for example an electromagnetic coil, and the electrical insulation expenditure is considerable. From a medical point of view, the relatively high stress placed upon the patient due to a high dose of acoustic energy, is undesirable.

It is an object of the present invention to design a shock wave source of the above-mentioned kind in such a way that the above-noted negative effects are reduced.

SUMMARY OF THE INVENTION

According to a first embodiment of the invention, this task is solved by placing between the focusing device and the seal diaphragm a substance having a high B/A value and an acoustic impedance less than or equal to that of water. The characteristic value B/A of the substance describes the deviation from linearity for the propagation of acoustic waves in a liquid or gaseous medium. For water at 20° C., the B/A value is 5.

According to a second embodiment of the invention, the task is solved by forming the focusing device from a substance having a high B/A value and an acoustic impedance which isless than that of water.

Suitable substances are castor oil, ethanol and benzene, which have B/A values of 10, 10.5 and 9, respectively.

With these measures, the build-up time of the pressure wave pulse on its way to the seal diaphragm is achieved much faster than with the customery water filling of the prepassage space. Thus, in the prepassage space a shorter build-up time of the pressure wave pulse is obtained. In this way it is possible to decrease the amplitude of the pressure pulse at the pressure source, as compared to a lithtriptor having a prepassage space filled with water.

Thus, at a given location between the focusing device and the seal diaphragm, with a suitable setting and inspite of the smaller amplitude of the pressure wave pulse generated by the pressure source, the same value of the quotient of amplitude to build-up time of the pressure wave pulse can exist as compared with the previously known water filling.

Since the pressure wave pulse needed at the pressure source is smaller, as a consequence a smaller electric voltage can be used for the generation of the pressure wave pulse. If the pressure source has an electric coil built into it, such as a shock wave tube, then the life expectancy of the coil is significantly increased. In addition, expenditure for insulation is reduced.

If a spark gap is used as the pressure source, than smaller electric voltage has a positive effect on the power consumption of the spark gap. Furthermore, due to the lower amplitude of the pulse, a smaller dose of acoustic energy stresses the body of the patient. This can lead to a reduction of potential side effects of lithotriptic treatment as, for instance, reduced dermal irritation at the site of the acoustical coupling.

These and other features and advantages of the invention will be apparent from the following description of the preferred embodiments, and from the claims.

For a fuller understanding of the present invention, reference should now be made to the following description of preferred embodiments of the invention and to their accompanying drawings.

DETAILED DESCRIPTION OF THE INVENTION

Figure 1:
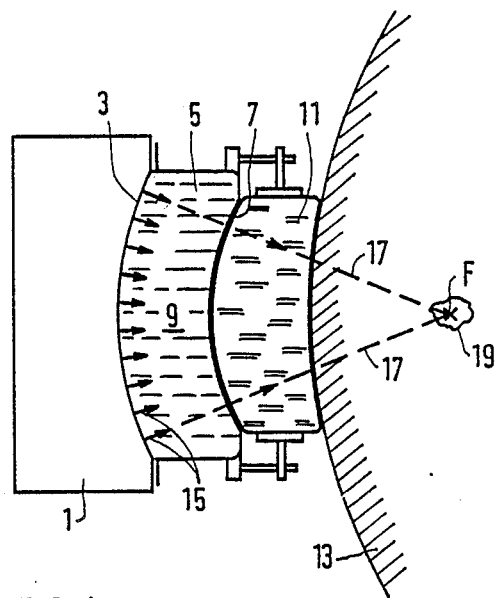
FIG. 1 illustrates a concave pressure source with prepassage space and coupling body constructed according to the principles of the invention.

In FIG. 1, a pressure source is labeled 1 which contains integral therewith a focusing device 3. Focusing device 3 is realized in the present case by the shape of pressure source 1. As known per se, the shaping can comprise a concave shaping of the radiating surface of a shock wave tube. Alternatively, it is possible to construct pressure source 1 and focusing device 3 as separate units. In this case, pressure source 1 would, for example, be a shock wave tube for the generation of a planar pressure wave pulse and focusing device 3 would be an acoustic lens or a reflector.

Adjoining pressure source 1 with integrated focusing device 3 is a prepassage space 5 which is delimted by a seal diagrahm 7. Seal diaphragm 7, together with pressure source 1, forms a space 9 which is filled with a fluid of high B/A ratio and an acoustic impedance less than or equal to that of water. On the front side of seal diaphragm 7 abuts a suitable coupling body 11 through which a pressure wave pulse is coupled into a patient 13 to be treated. The configuration of pressure source 1, prepassage space 5, and coupling body 11 results in a geometric focus F.

A pressure wave pulse 15 (indicated by small arrows) progresses along lines 17. At focus F is placed the concrement 19 of the patient 13 to be fragmented. By filling space 9 with a substance having a high B/A ratio and an acoustic impedance which is less than or equal to that of water, a fast build-up of the pressure wave pulse 15 in its travel through space 9 is achieved. Thus, it is possible to reduce the amplitude of pressure wave pulse 15 at focusing device 3 and thereby also at pressure source 1 as compared to using water and yet, at a given point between focus F and pressure source 1, achieve the minimum value of the quotient of amplitude and build-up time of the pressure wave pulse before the critical distance of approximately one-half wavelength, so as to obtain the information of a shock wave. The critical distance results from a discontinuance of the focusing due to a diffraction limitation of the pressure wave pulse; with such discontinuance, a shock wave can not form at the focus.

By reducing the amplitude of pressure wave pulse 15 in the area of focusing device 3, and thereby also at pressure source 1, an increase in the life expectancy of pressure source 1 from the point of view of the equipment is achieved as well as a reduced electric insulation expenditure in electric pressure source 1. Simultaneously, stresses placed on patient 13 due to the acoustic energy is reduced. Thus, the degree of effectiveness of the entire shock wave source is increased.

Figure 2:
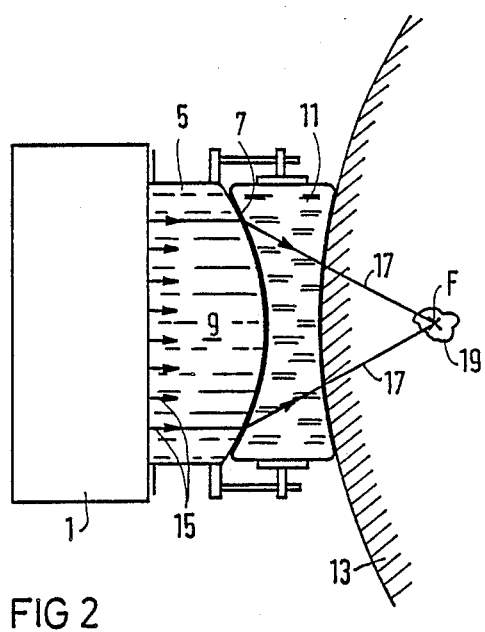
FIG. 2 illustrates pressure source with a convex seal diaphragm and coupling through a gelatineous body, constructed in accordance with the principles of the invention.

In FIG. 2 identical construction elements are labeled with the same reference numbers as in FIG. 1. Here, pressure source 1 generates a planar pressure wave pulse 15. Adjacent to pressure source 1 is a seal diaphragm 7, which forms a prepassage space 5, thereby enclosing a space 9. Space 9 is preferably filled with ethanol. The frontal surface of seal diaphragm 7 is convex. Adjacent to this convex frontal surface is a correspondingly spaced coupled body 11 of a suitable material, for instance a gel, having an acoustic impedance which is matched to the body of the patient. The free frontal surface of coupling body 11 is placed against the patient 13. The entire configuration has a geometric focus F in which is placed concrement 19. Pressure wave pulse 15 travels through space 9 and coupling body 11 as indicated with lines 17.

The use of ethanol in space 9, instead of water, considerably accelerates the build-up of pressure wave pulse 15 as compared with water. Thus, the amplitude of the initial pressure wave pulse 15 required for the formation of a shock wave in the focus F is reduced by approximately one-half.

Thus, there has been shown and described novel apparatus for a shock wave source which fulfills all the objects and advantages sought therefore. Many changes, modifications, variations and other uses and applications of the subject invention will, however, become apparent to those skilled in the art after considering this specification and the accompanying drawings which disclose a preferred embodiment thereof. For example, an ethanol prepassage 9 in combination with a flat concave pressure source 1 (not shown) and a planar separation surface to the coupling body 11 would act similarly with respect to focusing as planar pressure source 1 with convex frontal area at seal diaphragm 7 (as shown in FIG. 2).

Another use of the described shock wave source is the treatment with shock waves of tumors which are palpable or inside the body. All such changes, modifications, variations and other uses and applications which do not depart from the spirit and scope of the invention are deemed to be covered by the invention which is limited only by the claims which follow.

What we claim is:

1. A shock wave source, particularly useful for a lithotriptor, comprising:

a pressure source for the generation of a pressure wave pulse having a direction of propagation;

a coupling body having an output adapted to be coupled to a body of a patient, said coupling body comprising material having an acoustic impedance value matched to that of the body of the patient;

a seal diaphragm for acoustically coupling said pressure wave pulse into said coupling body;

said seal diaphragm having a front wall disposed at a distance, in the direction of propagation of the pressure wave pulse, from the pressure source and in contact with said coupling body;

said seal diaghragm and said pressure source enclosing a space containing a substance having a B/A nonlinearity parameter value higher than that of water and an acoustic impedance value which is less than or equal to that of water;

said substance being acoustically coupled to both the pressure source and the seal diaphragm; and said front wall of said seal diaphragm being shaped so as to cause focusing of the pressure wave pulse generated by the pressure source.

2. A shock wave source, particularly useful for a lithotriptor, comprising:

a pressure source for the generation of a pressure wave pulse having a direction of propagation;

a coupling body having an output adapted to be coupled to a body of a patient, said coupling body comprising material having an acoustic impedance value match to that of the body of the patient;

a seal diaphragm for acoustically coupling said pressure wave pulse into said coupling body;

said seal diaphragm having a curved front wall facing said pressure source disposed at a distance, in the direction of propgation of the pressure wave pulse, from the pressure source and in contact with said coupling body;

said seal diaphragm and said pressure source enclosnig a space containing a liquid having a B/A nonlinearity parameter value higher than that of water and an acoustic impedance value which is less than or equal to that of water;

said liquid being acoustically coupled to both the pressure source and the seal diaphragm; and said front wall of said seal diaphragm being curved so as to cause focusing of the pressure wave pulse generated by the pressure source.

3. A shock wave source according to claim 2, wherein said liquid is selected from the group consisting of castor oil, ethanol, and benzene.

* * * * *